(12) United States Patent
Connors, III

(10) Patent No.: US 6,295,989 B1
(45) Date of Patent: Oct. 2, 2001

(54) ICA ANGIOPLASTY WITH CEREBRAL PROTECTION

(75) Inventor: John J. Connors, III, New Orleans, LA (US)

(73) Assignee: Arteria Medical Science, Inc., San Francisco, CA (US)

(*) Notice: Subject to any disclaimer, the term of this patent is extended or adjusted under 35 U.S.C. 154(b) by 0 days.

(21) Appl. No.: 09/018,365

(22) Filed: Feb. 4, 1998

Related U.S. Application Data

(60) Provisional application No. 60/038,040, filed on Feb. 6, 1997, provisional application No. 60/037,225, filed on Feb. 6, 1997, provisional application No. 60/038,039, filed on Feb. 6, 1997, and provisional application No. 60/037,226, filed on Feb. 6, 1997.

(51) Int. Cl.⁷ ..................................................... A61B 19/00
(52) U.S. Cl. ............................................................ 128/898
(58) Field of Search ................................. 128/898; 623/1, 623/11, 66; 604/53, 52, 54, 49, 48, 93, 96–104; 600/18; 606/191

(56) References Cited

U.S. PATENT DOCUMENTS

| | | |
|---|---|---|
| 3,726,269 | 4/1973 | Webster, Jr. . |
| 4,033,331 | 7/1977 | Guss et al. . |
| 4,169,464 | 10/1979 | Obrez . |
| 4,573,966 | 3/1986 | Weikl et al. . |
| 4,921,478 * | 5/1990 | Solano et al. ........................... 604/53 |
| 4,925,445 | 5/1990 | Sakamoto et al. . |
| 4,935,017 | 6/1990 | Sylvanowicz . |
| 5,120,323 | 6/1992 | Shockey et al. . |
| 5,163,906 | 11/1992 | Ahmadi . |
| 5,199,951 | 4/1993 | Spears . |
| 5,203,776 | 4/1993 | Durfee . |
| 5,215,540 | 6/1993 | Anderhub . |
| 5,219,355 | 6/1993 | Parodi et al. . |
| 5,267,982 | 12/1993 | Sylvanowicz . |
| 5,290,229 | 3/1994 | Paskar . |
| 5,304,131 | 4/1994 | Paskar . |
| 5,342,306 | 8/1994 | Don Michael . |
| 5,348,545 | 9/1994 | Shani et al. . |
| 5,368,566 | 11/1994 | Crocker . |
| 5,389,090 | 2/1995 | Fischell et al. . |
| 5,458,574 | 10/1995 | Machold et al. . |
| 5,462,529 | 10/1995 | Simpson et al. . |
| 5,480,380 | 1/1996 | Martin . |
| 5,484,412 | 1/1996 | Pierpont . |

FOREIGN PATENT DOCUMENTS

| | | |
|---|---|---|
| 0277366A1 | 8/1988 | (EP) . |
| 0339799B1 | 10/1994 | (EP) . |
| WO96/26758 | 9/1996 | (WO) . |

OTHER PUBLICATIONS

Theron et al., Carotid Artery Stenosis: Treatment with Protected Balloon Angioplasty and Stent Replacement, Radiology, (Dec. 1996), 201(3), 627–36.*

* cited by examiner

Primary Examiner—Dinh Nguyen
(74) Attorney, Agent, or Firm—Fish & Neave; Nicola A. Pisano

(57) ABSTRACT

A method of performing an operation including angioplasty of the internal carotid artery which includes blocking blood flow in the internal carotid artery, performing the angioplasty while the blood flow is blocked in the internal carotid artery, and reversing flow in the internal carotid artery after the angioplasty has been performed to wash material loosened during the angioplasty out of the internal carotid artery. Normal flow in the internal carotid artery is restored after the loosened material is washed out of the internal carotid artery.

1 Claim, 22 Drawing Sheets

ICA ANGIOPLASTY WITH CEREBRAL PROTECTION

CROSS-REFERENCE TO RELATED APPLICATIONS

This application claims priority of my U.S. Provisional Patent Application Serial Nos. 60/038,040; 60/037,226; 60/037,225; and 60/038,039, all filed Feb. 6, 1997 and all incorporated herein by reference. This application also claims priority of my U.S. Provisional Patent Application also filed on Feb. 6, 1997 with the four above-mentioned provisional patent applications and entitled "ICA ANGIOPLASTY WITH CEREBRAL PROTECTION" and bearing attorney docket number V97004US (16064/4). That application is also incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to internal carotid artery (ICA) angioplasty with cerebral protection. More particularly, the present invention relates to a system for conducting angioplasty while minimizing risk of strokes.

2. General Background of the Invention

When angioplasties are performed, sometimes plaque gets dislodged and travels into the brain, sometimes causing strokes.

The following references are hereby incorporated by reference:

Guide catheters these days are introduced generally through the body though a large sheath. There are now some guide catheters which are introduced with a small thin dilator that leads them over a wire into the body, and one ends up with a guide catheter in the body that was gotten in there loaded over the little dilator. These are then in a location not applicable to guide catheter use. For use in a branch vessel, they have to be led by a previously placed selective catheter and/or a guide wire.

U.S. Pat. Nos. 3,726,269; 4,033,331; 4,169,464; 4,573,966; 4,925,445; 4,935,017; 5,120,323; 5,163,906; 5,199,951; 5,203,776; 5,215,540; 5,219,355; 5,267,982; 5,290,229; 5,304,131; 5,342,306; 5,348,545; 5,368,566; 5,389,090; 5,458,574; 5,462,529; 5,480,380; 5,484,412; European Patent Specification Publication Nos. 0 339 799 B1 and 0 277 366 A1 and PCT International Application Publication No. WO 96/26758.

BRIEF SUMMARY OF THE INVENTION

The apparatus of the present invention solves the problems confronted in the art in a simple and straightforward manner. What is provided is a method of performing an operation including angioplasty of the internal carotid artery comprising the following steps: (a) blocking blood flow in the internal carotid artery; (b) performing the angioplasty while the blood flow is blocked in the internal carotid artery; (c) reversing flow in the internal carotid artery after the angioplasty has been performed to wash material loosened during the angioplasty out of the internal carotid artery; and (d) restoring normal flow in the internal carotid artery.

Also provided is a guide catheter system which can be inserted into a patient without a sheath, thus allowing the use of large guide catheters without a corresponding larger hole in the vessel wall.

The present system allows selective placement of a guide catheter in one step, eliminating the need for a sheath, selective diagnostic catheter, and exchange wire.

The entire process of guide catheter introduction is one process, thus much faster. The unit is placed over a standard guide wire through the skin into the vasculature. The lack of need for a separate sheath system saves this step from the introducer.

The eventual target vessel for the guide catheter is selected with a catheter/dilator specifically designed for that purpose (the inner "dilator"). This allows optimal design capabilities for the guide catheter due to the fact that it will not have to function as a selecting catheter at the same time.

The lack of need for a separate diagnostic catheter to pre-select the intended vessel saves the step of placing a diagnostic catheter into the intended location, placing an exchange wire, pulling the selective catheter, and then placing a guide catheter over this exchange wire.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
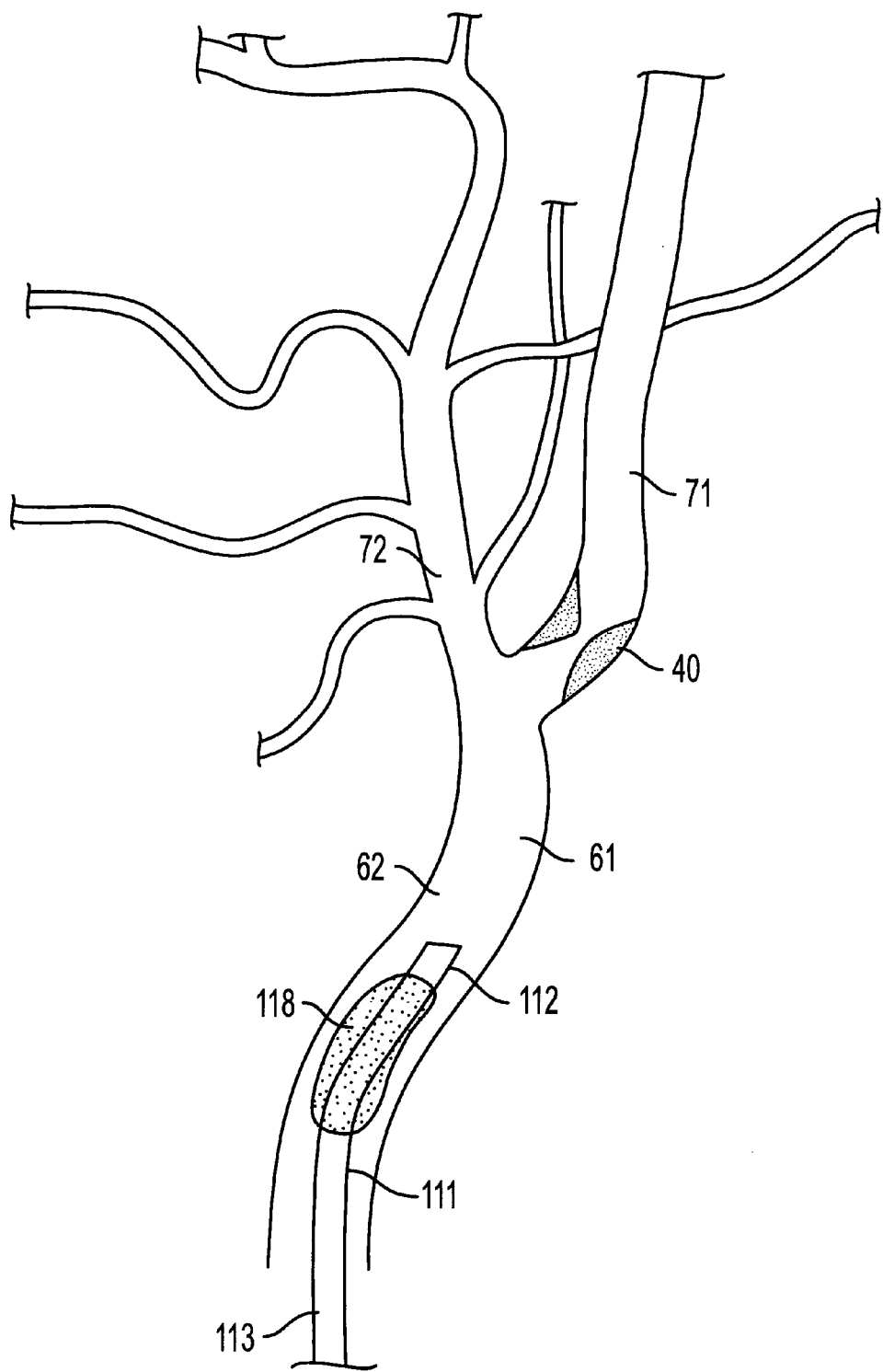
FIG. 1 shows initial placement of the flow control guide catheter.

In FIG. 1 initial placement of the flow control guide catheter 111 has been made, but the balloon 118 has not been inflated; antegrade flow is still present in the common carotid artery 61 and internal and external carotid arteries 71, 72.

Figure 2:
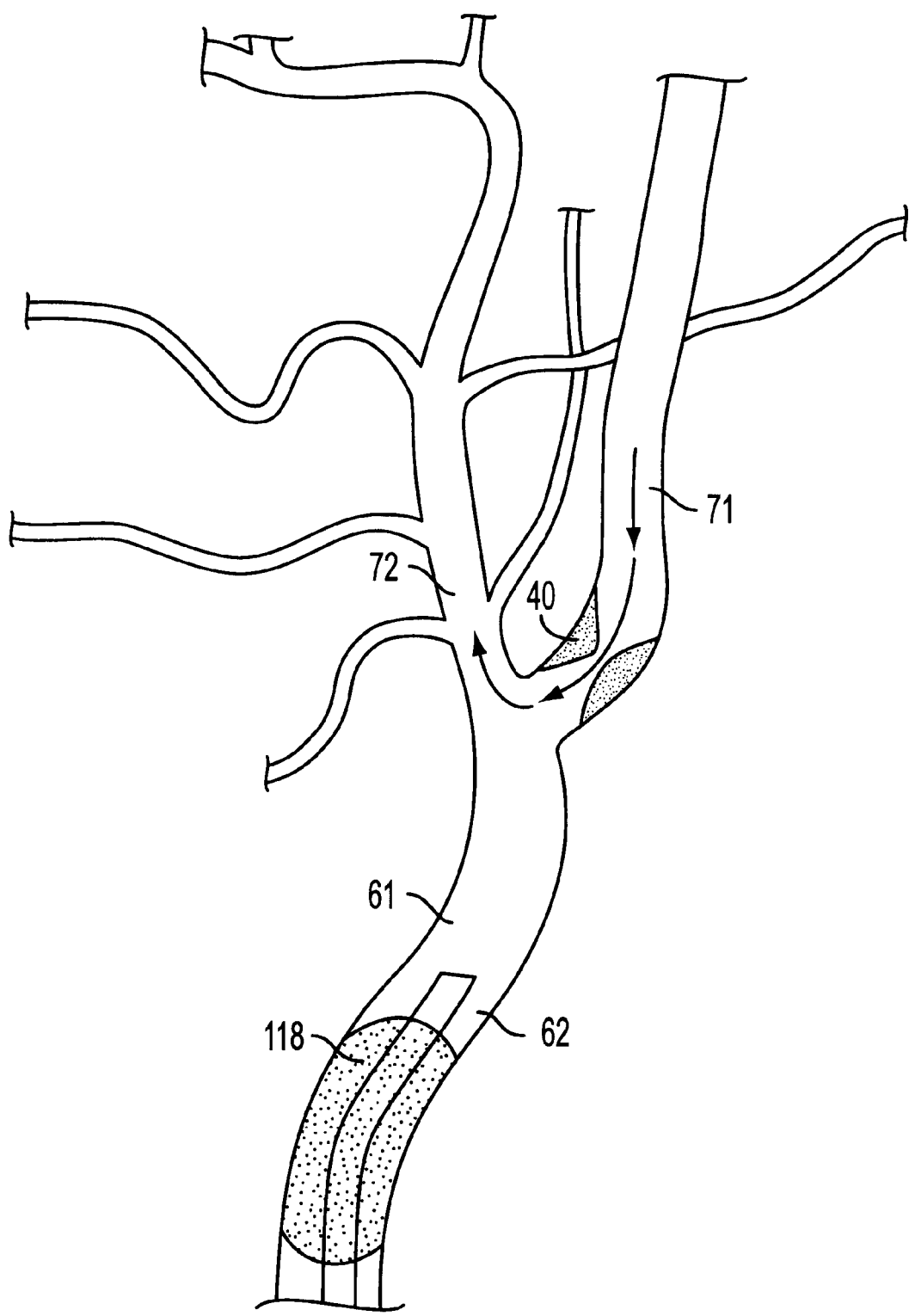
FIG. 2 shows the guide catheter balloon inflated.

In FIG. 2, inflation of the guide catheter balloon 118 stops flow in the common carotid artery 61 and reverses flow in the internal carotid artery 71. The high pressure intracranial vascular system will supply the low pressure sump of the external carotid artery 72.

Figure 3:
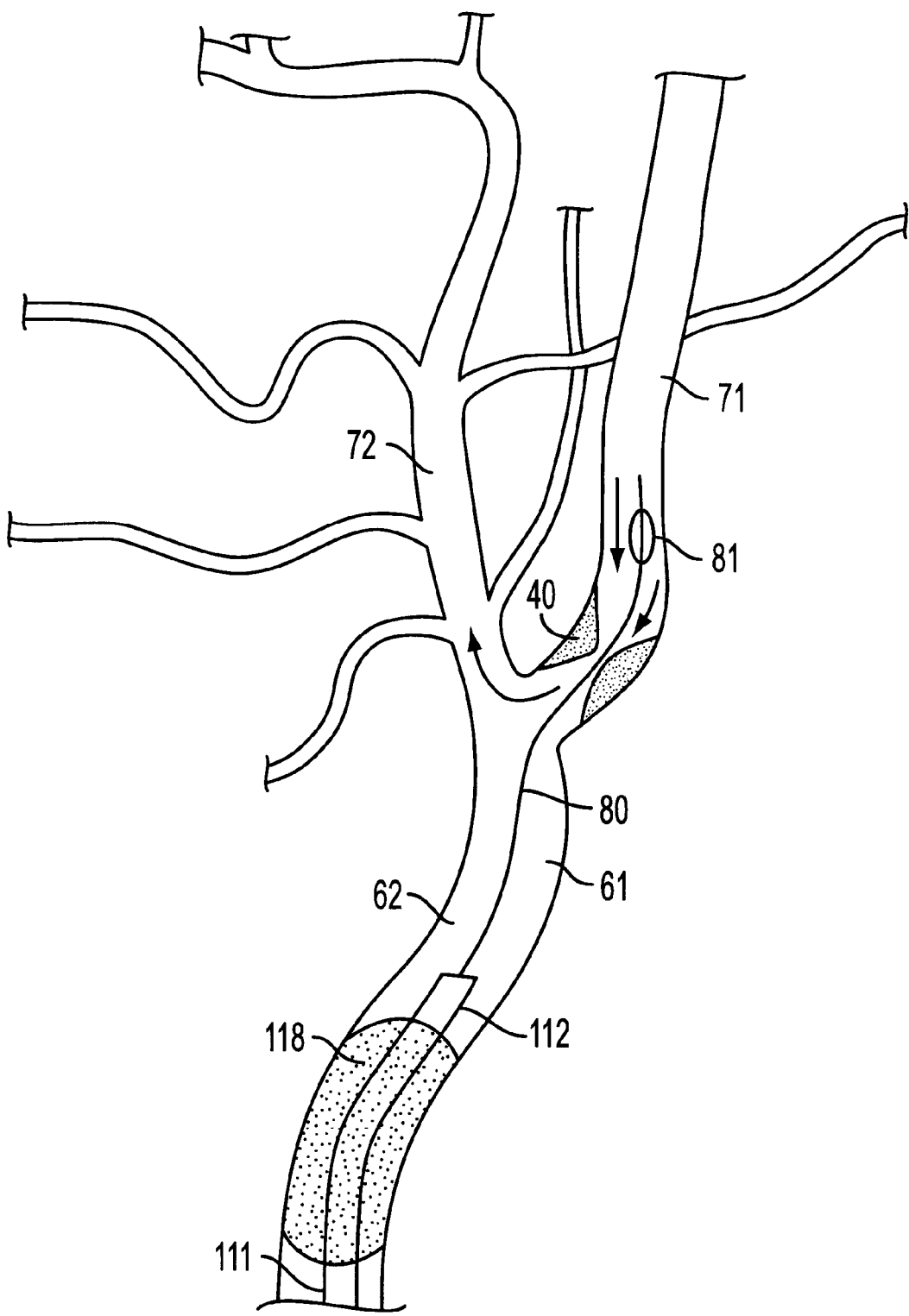
FIG. 3 shows a soft tipped "wire with a balloon" being advanced through the lesion.

In FIG. 3, while flow reversal is occurring, a soft tipped "wire with a balloon" 80 is advanced safely through the lesion 40; any material displaced during passage will flow in a retrograde course out the external carotid artery 72.

Figure 4:
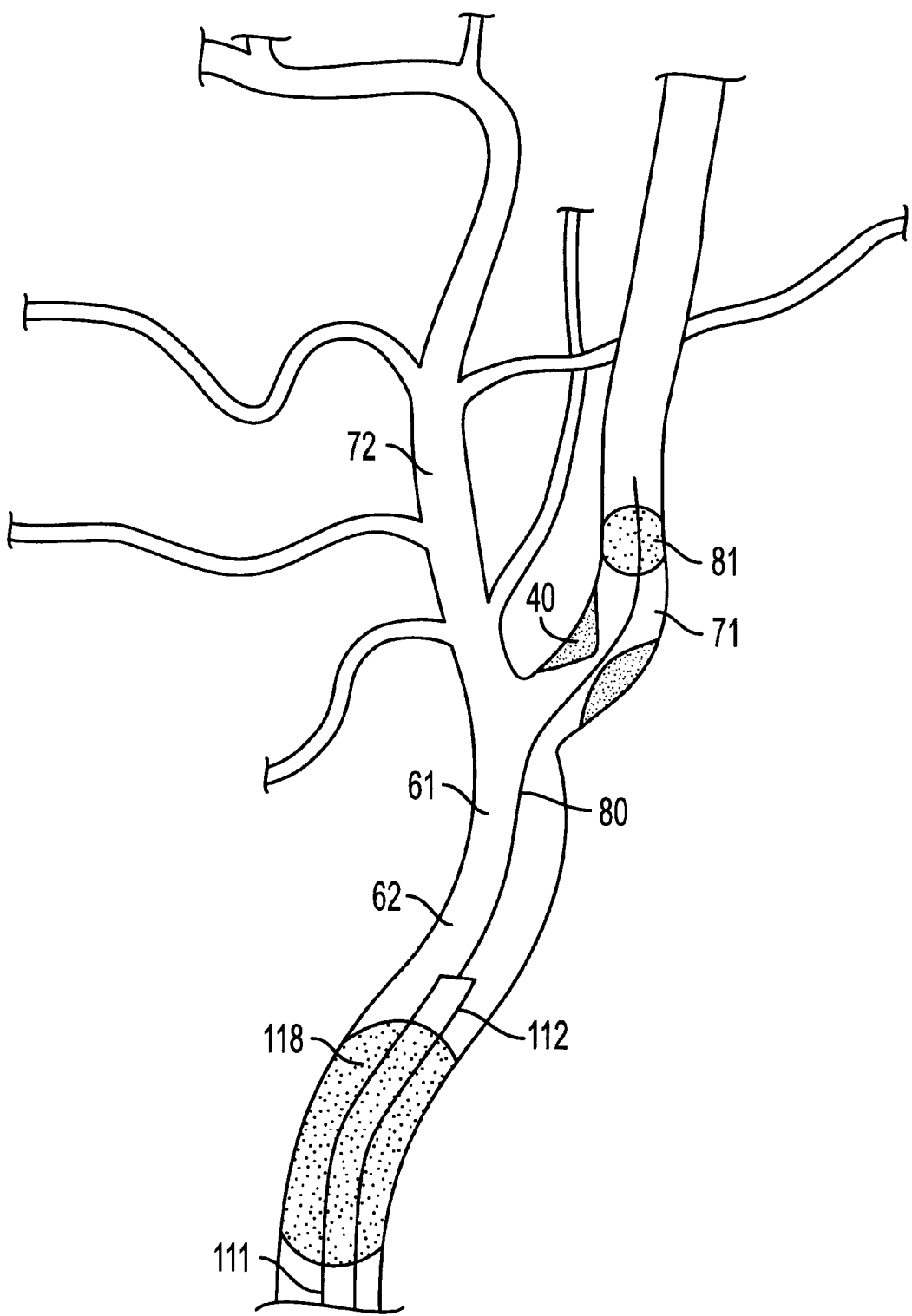
FIG. 4 shows the distal balloon inflated.

In FIG. 4, the distal balloon 81 is inflated, stopping all flow in the internal carotid artery 71.

Figure 5:
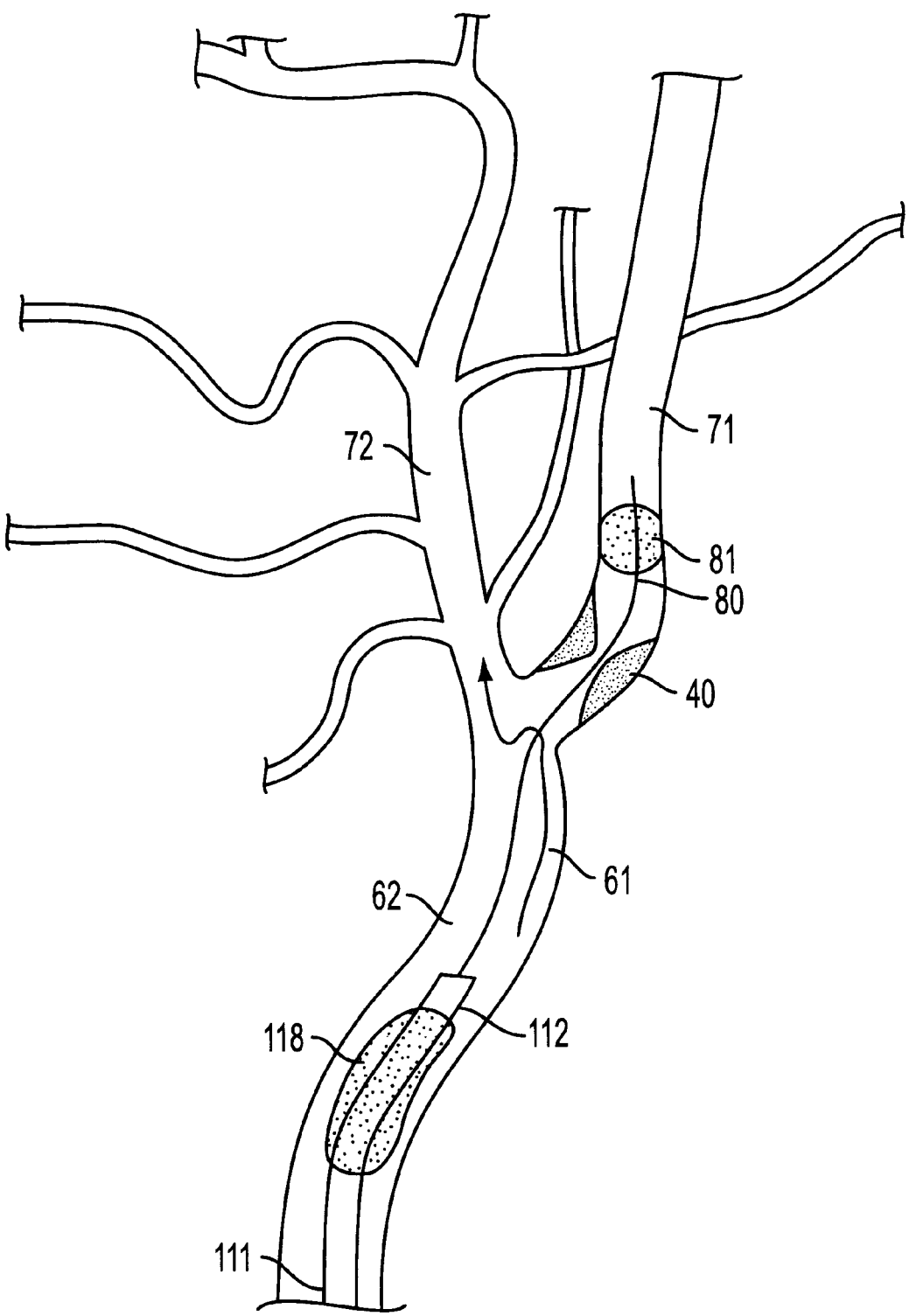
FIG. 5 shows the guide catheter balloon deflated.

In FIG. 5, the guide catheter balloon 118 is deflated, washing out the stagnant blood and debris in the region of the stenosis 40.

Figure 6:
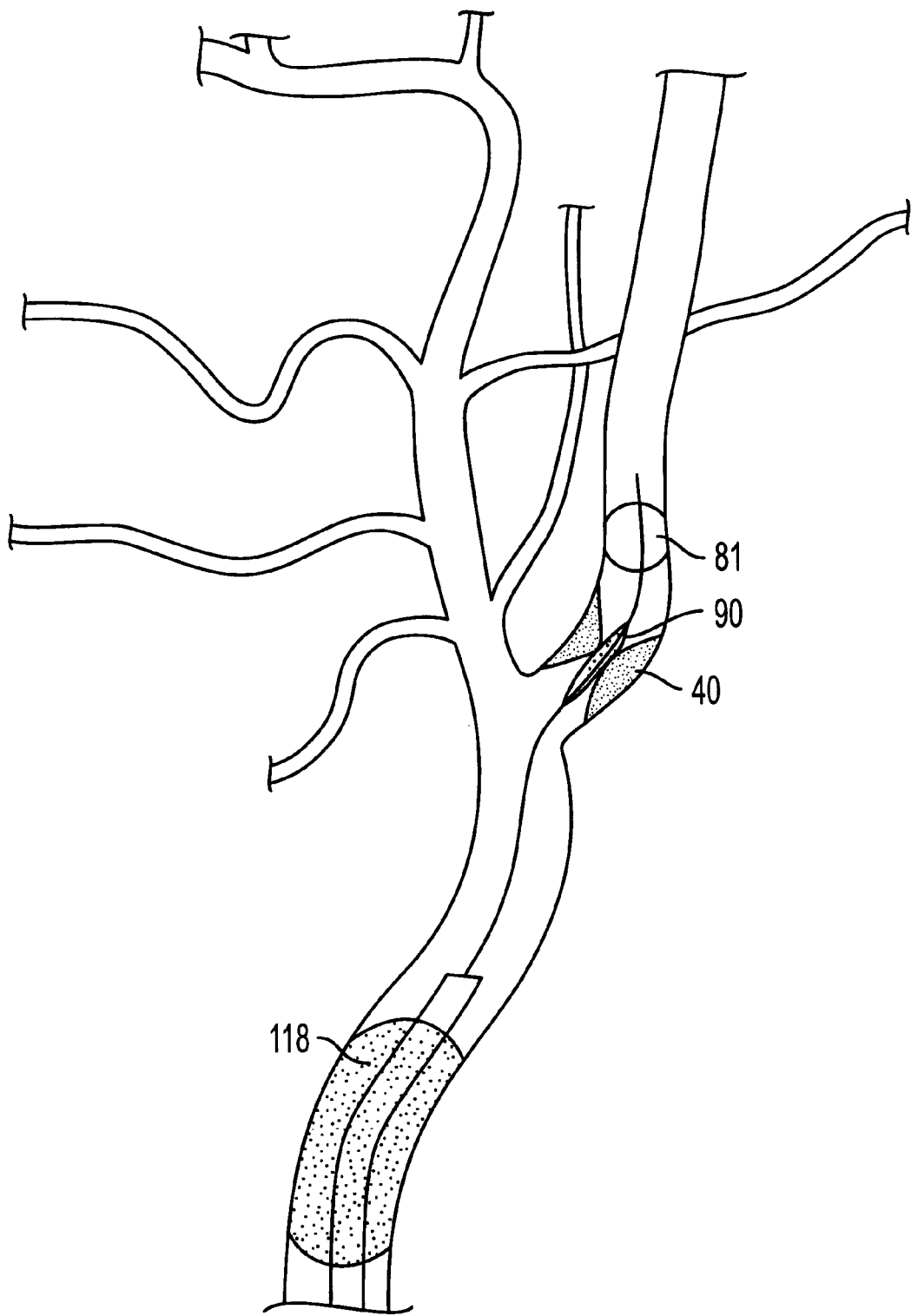
FIG. 6 show both balloons inflated.

In FIG. 6, both balloons 81, 118 are inflated and the angioplasty catheter 90 is delivered safely to its intended location.

Figure 7:
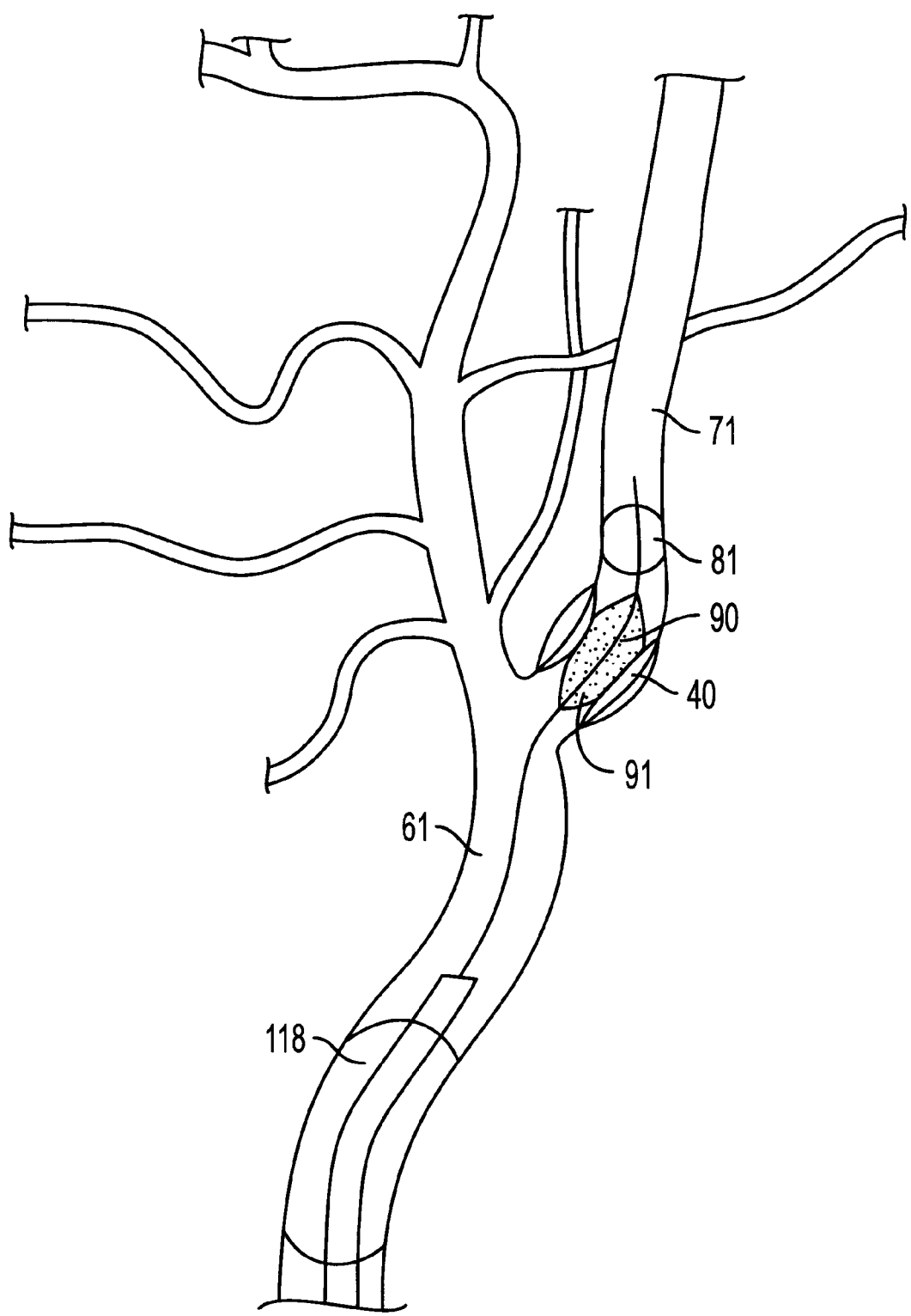
FIG. 7 shows the angioplasty being performed.

In FIG. 7, the angioplasty is performed while flow is arrested in the common carotid 61 and internal carotid 71 arteries.

Figures 8, 9:
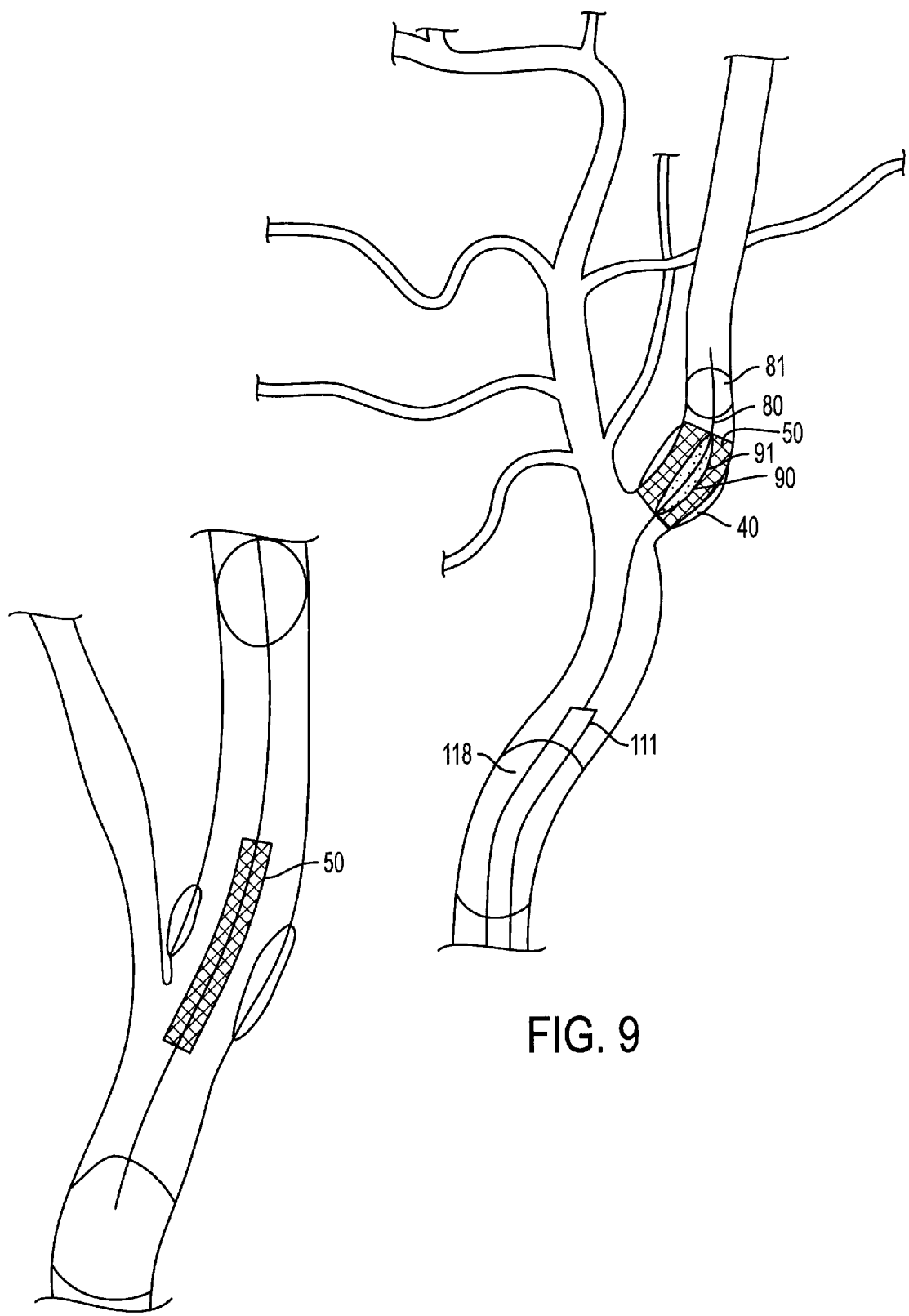
FIG. 8 shows a stent being delivered into the closed system.
FIG. 9 shows the stent being deployed.

In FIG. 8, after initial angioplasty, a stent 50 is delivered into the closed system, again with both the distal and proximal flow occluded.

In FIG. 9, the stent 50 is safely deployed under flow arrest.

Figure 10:
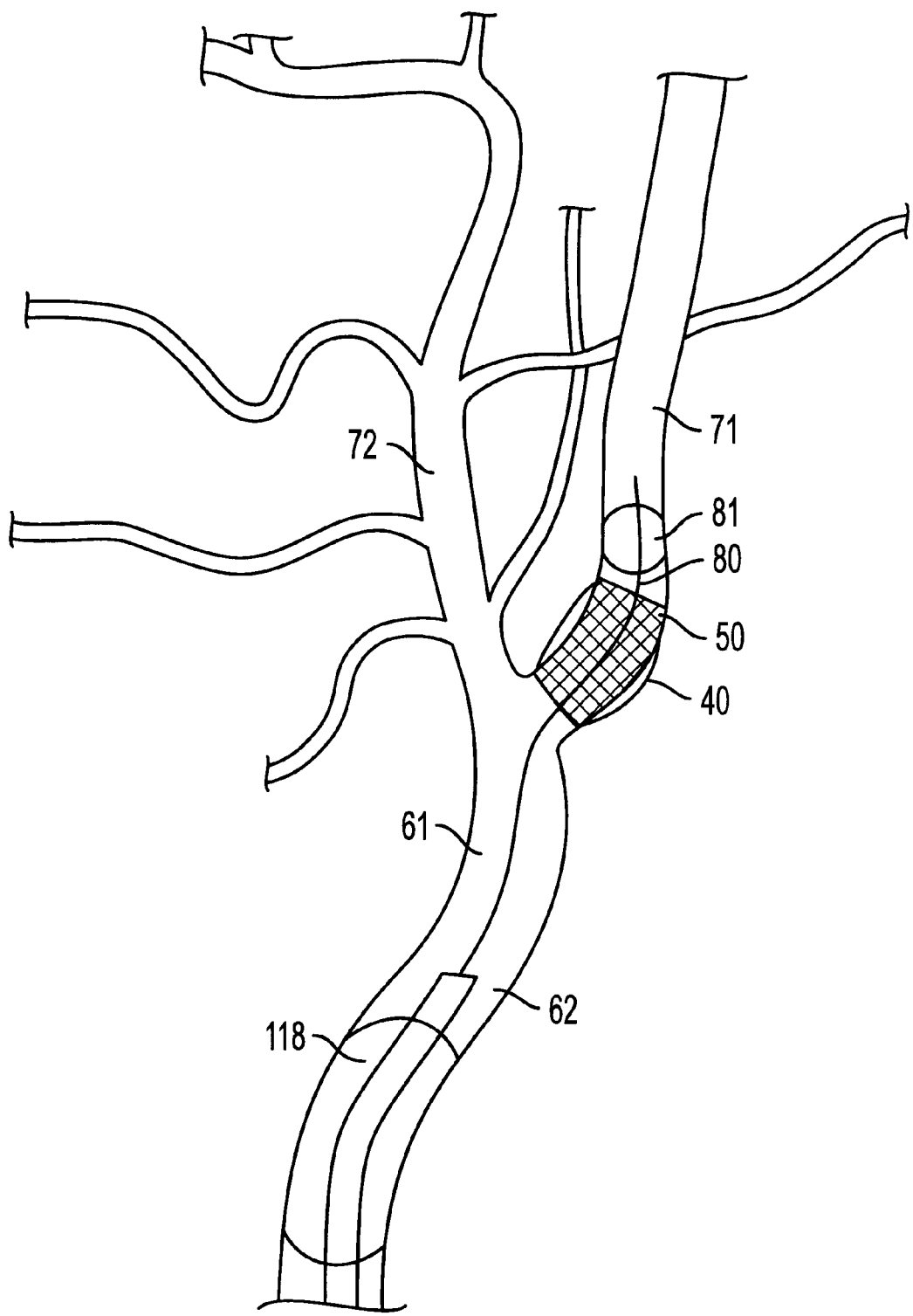
FIG. 10 shows the stent in place.

In FIG. 10, the angioplasty catheter 90 is withdrawn, leaving the stent 50 in place with flow arrested in the carotid arteries 61, 71, 72.

Figure 11:
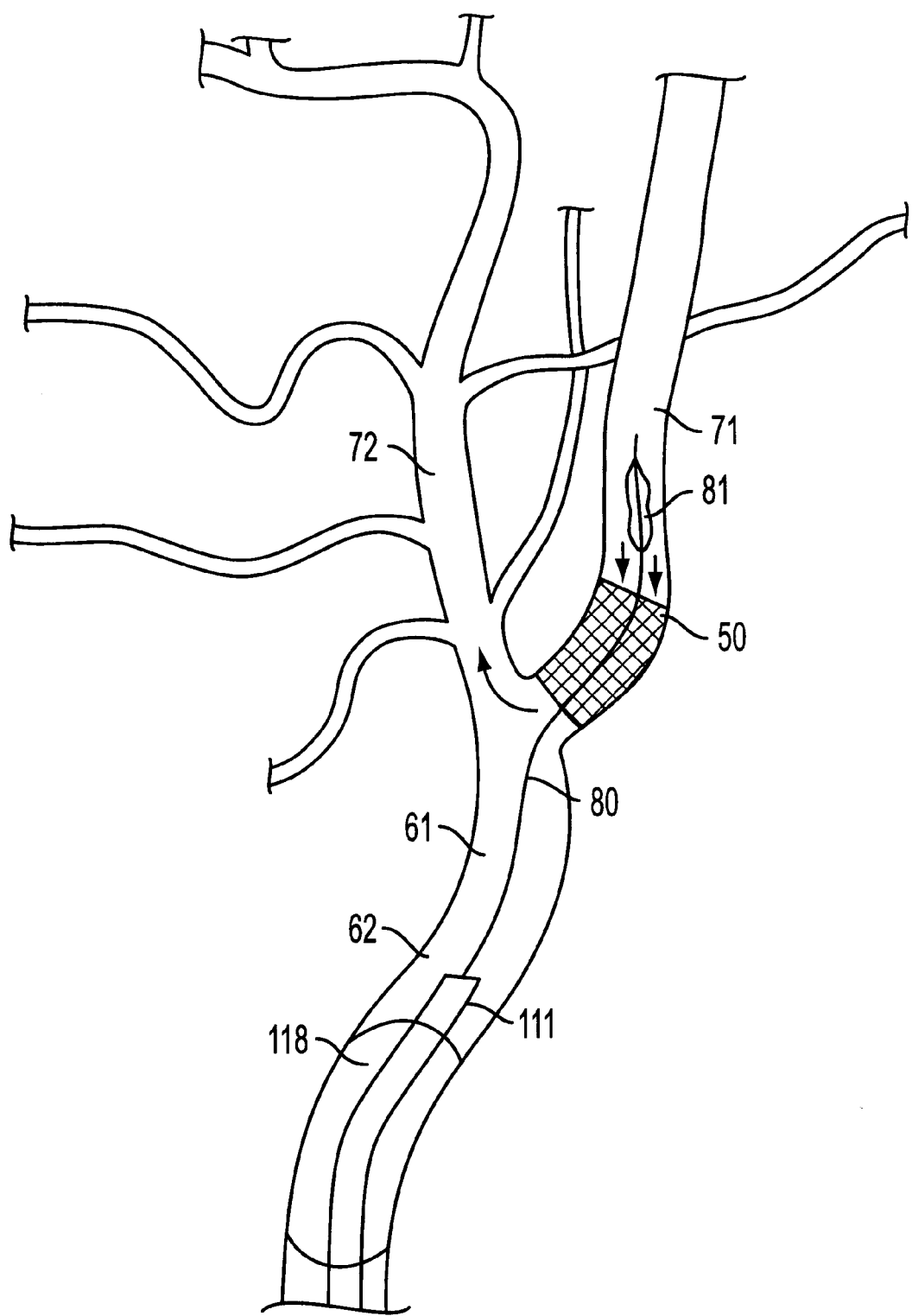
FIG. 11 show the distal balloon deflated.

In FIG. 11, the distal balloon 81 is deflated, allowing reversal of flow again in the internal carotid artery 71. This allows any retained material to be washed into the external carotid artery 72 again.

Figure 12:
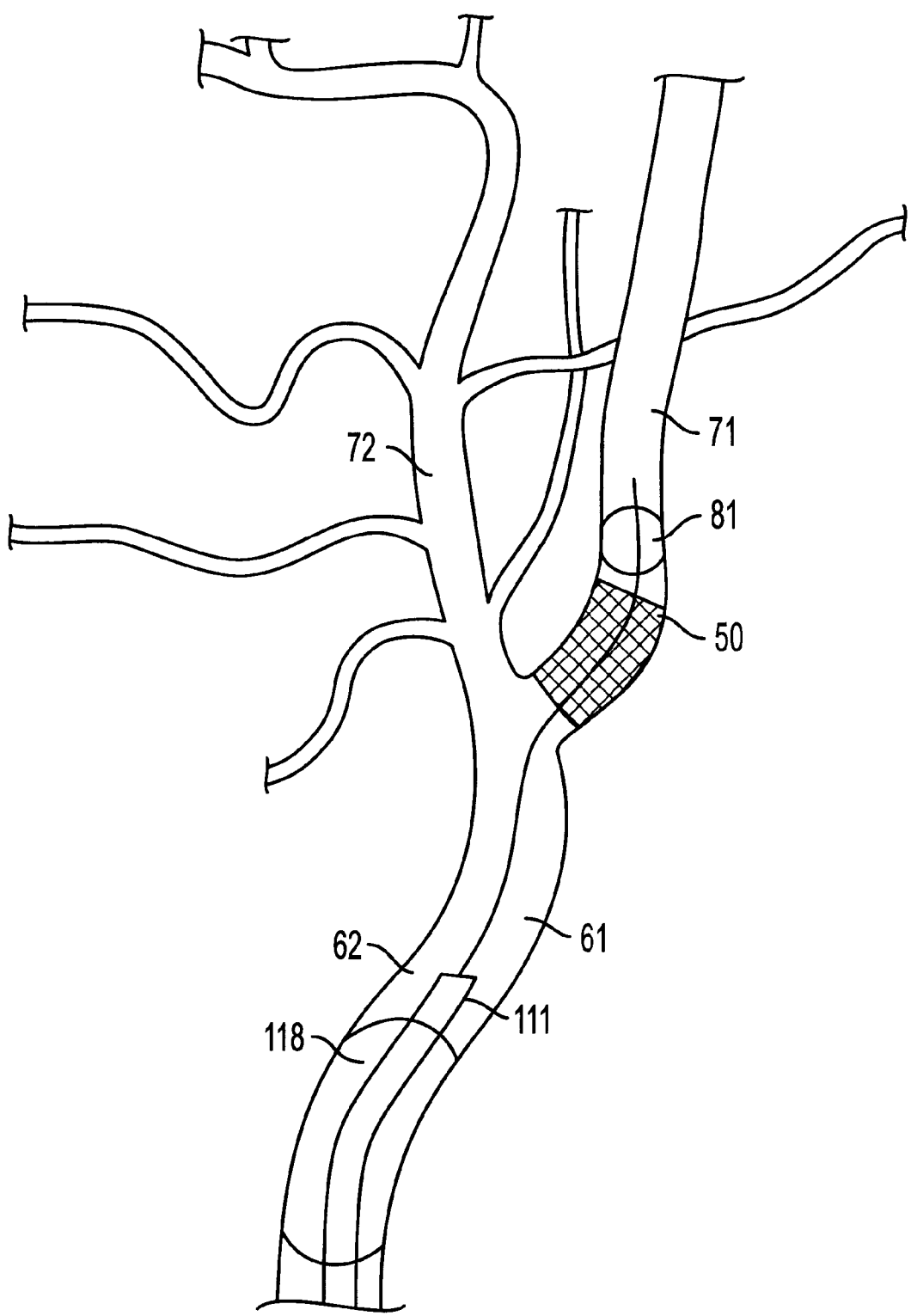
FIG. 12 show the distal balloon re-inflated.

In FIG. 12, the distal balloon 81 is re-inflated, again stopping flow in the internal carotid artery 71.

Figure 13:
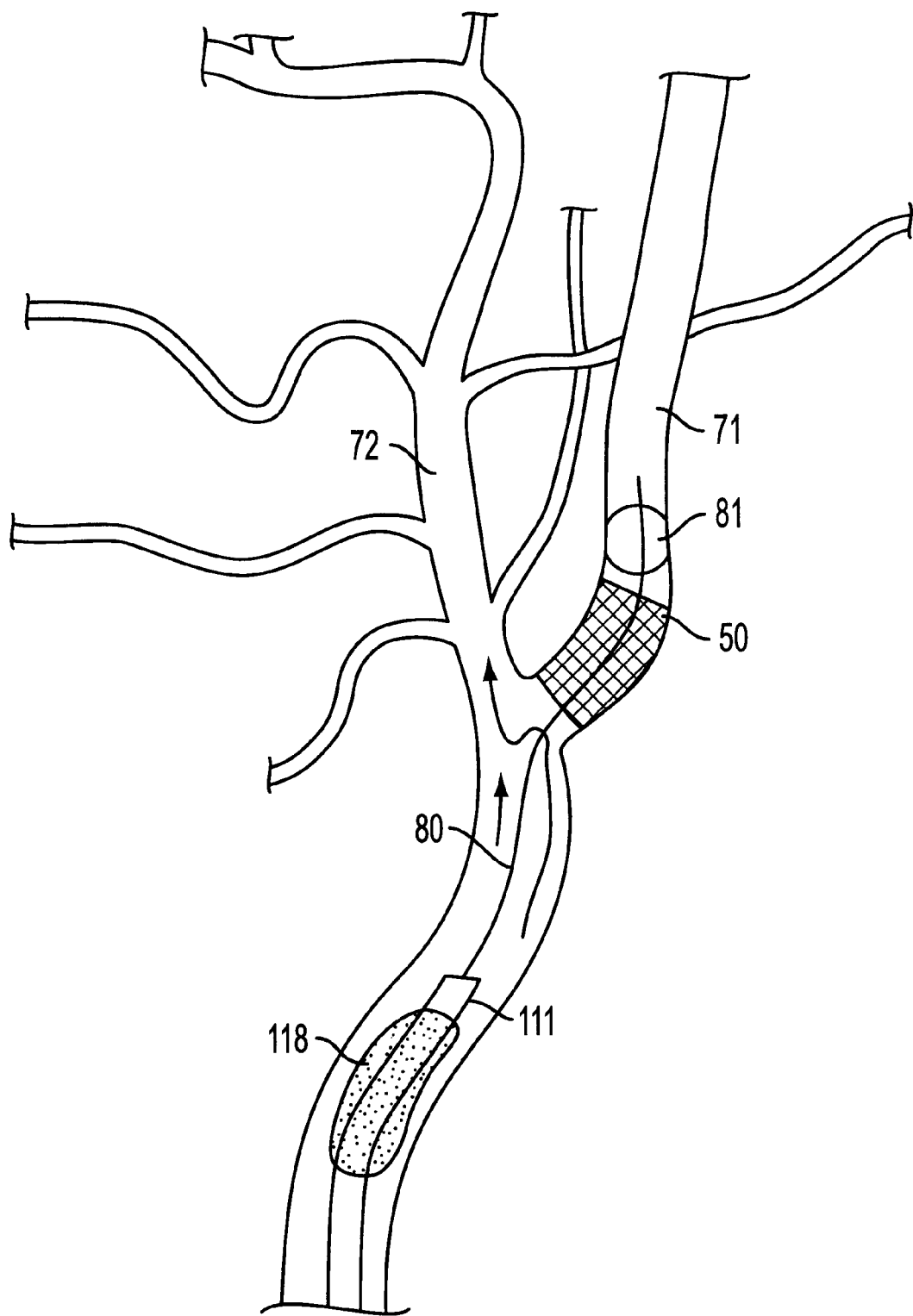
FIG. 13 shows the proximal balloon deflated.

In FIG. 13, the proximal balloon 118 is deflated. This allows high pressure antegrade flow into the external carotid artery 72 and allows contrast injection through the inner lumen of the guide catheter 111. Evaluation of the result of the angioplasty/stent is now possible. Any retained material is now forcefully washed out of the system into the external carotid artery 72.

Figure 14:
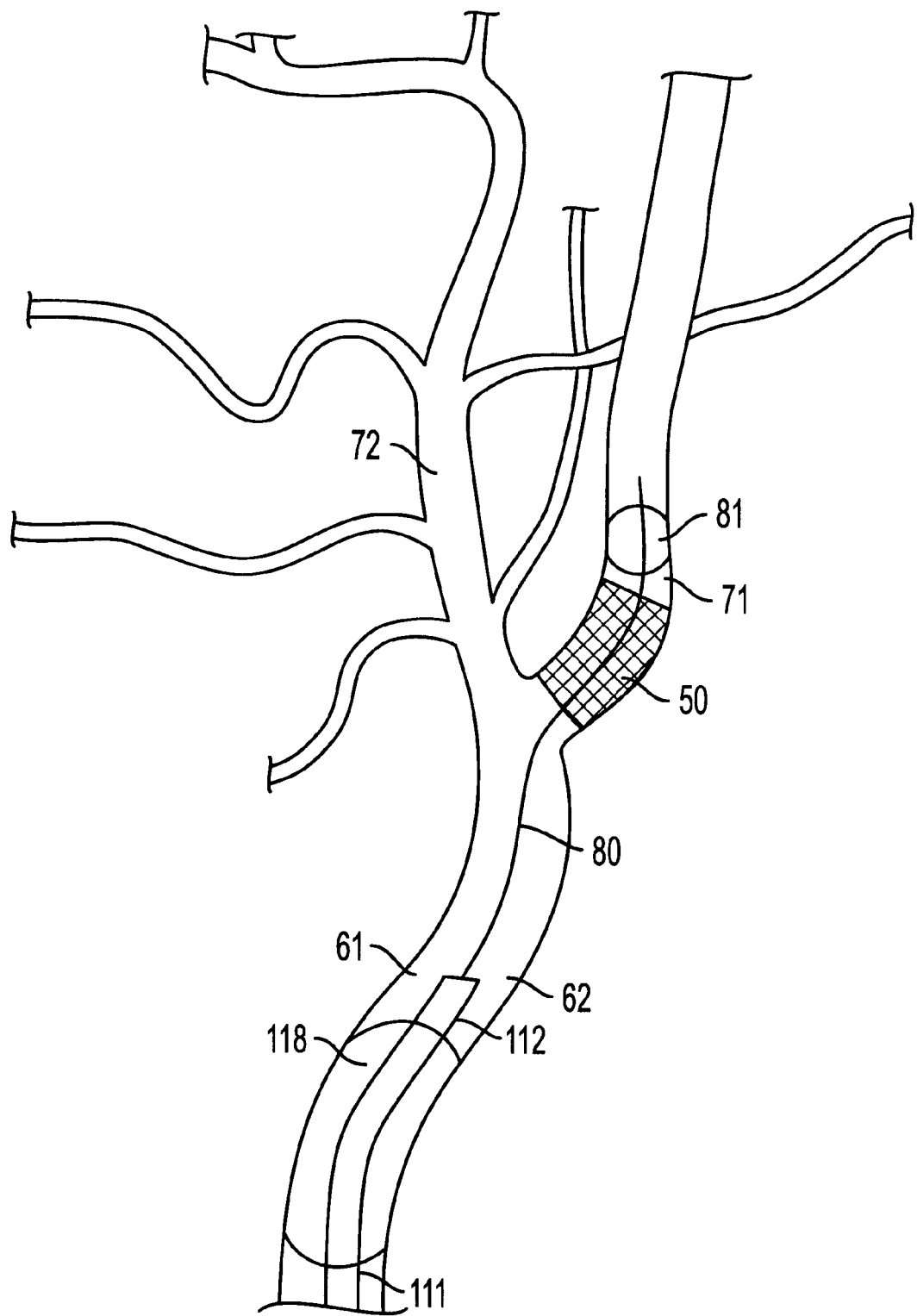
FIG. 14 shows the proximal balloon inflated.

In FIG. 14, the proximal balloon 118 is again inflated.

Figure 15:
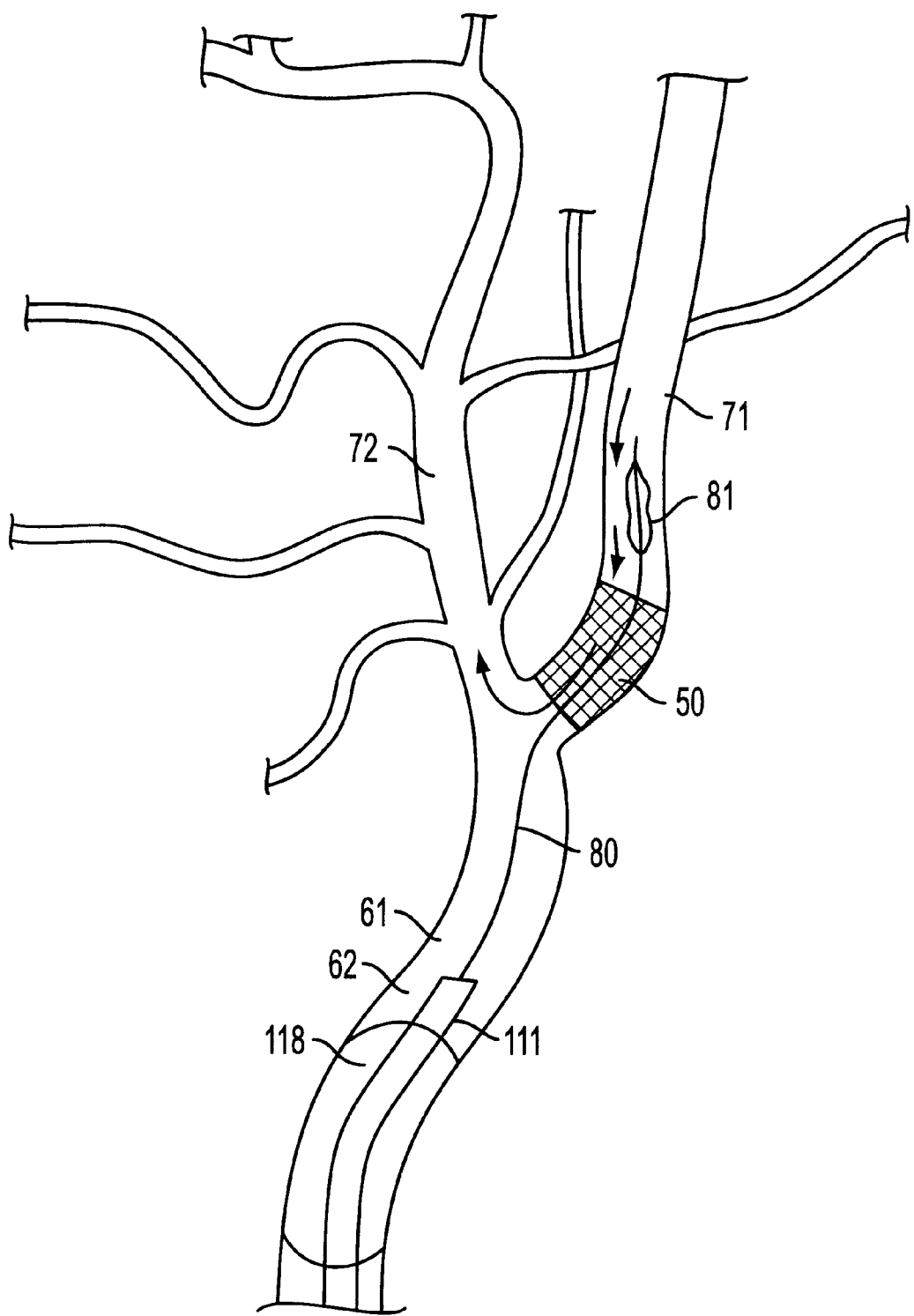
FIG. 15 shows the distal balloon deflated.

In FIG. 15, the distal balloon 81 is deflated. While flow is again reversed in the internal carotid artery 71, the distal wire/balloon 80 is safely withdrawn, again with no chance of dislodging any material into the intracranial flow.

Figure 16:
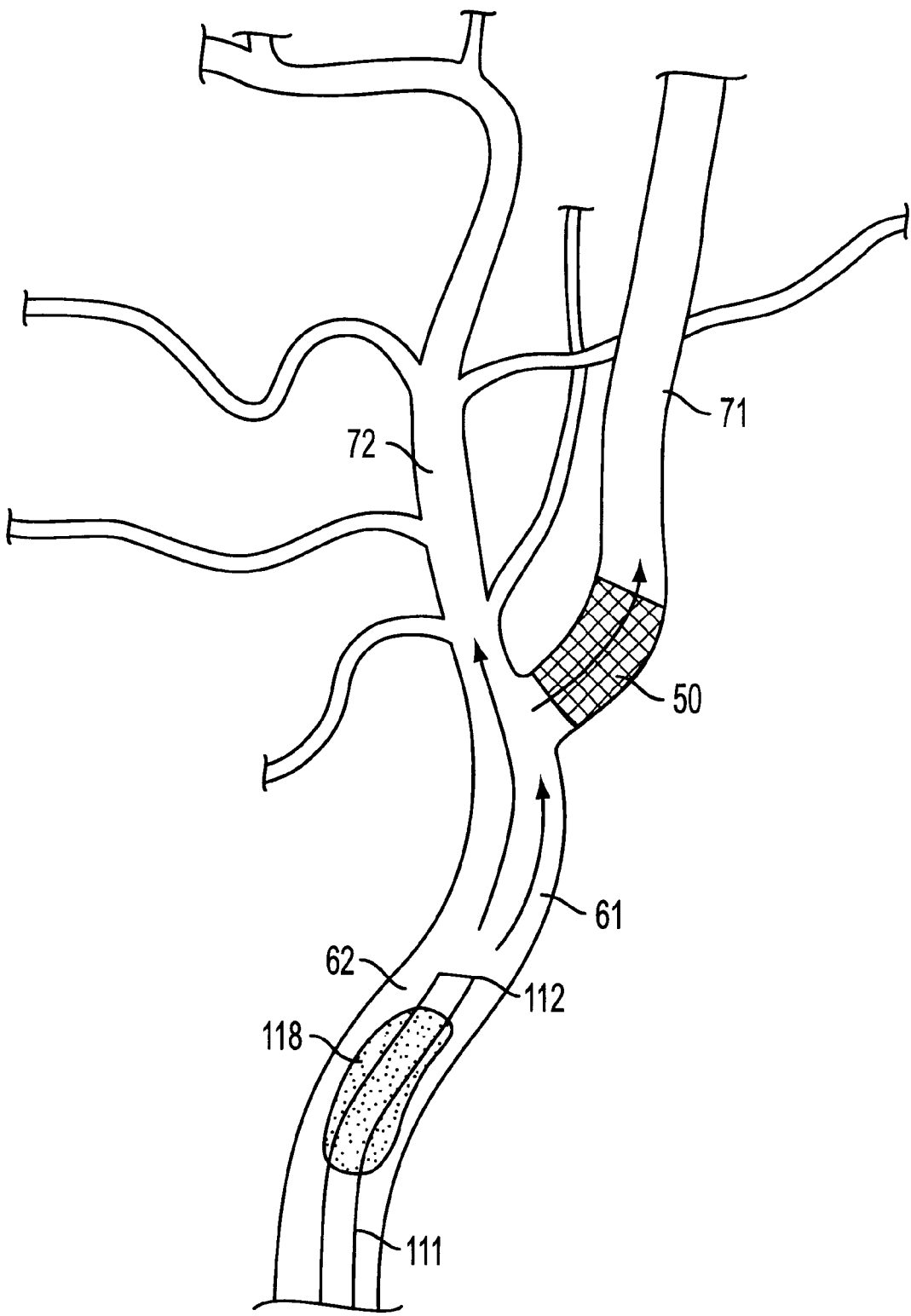
FIG. 16 shows the guide catheter balloon deflated.

In FIG. 16, once the inner wire/balloon 80 has been withdrawn, the guide catheter balloon 118 is deflated, allowing final contrast injection through the guide catheter lumen to evaluate the results.

This is also the technique of choice for internal carotid artery stenting due to its excellent cerebral protection.

1. Select the common carotid artery 61 using a selective diagnostic cerebral catheter; evaluate the path available to the angioplasty site.

2. Exchange the diagnostic catheter for a flow control guide catheter utilizing a safe "neuro" exchange wire. (Instead of the first two steps listed above, one could instead use the flow control guide catheter 111 of the present invention which is a modified version of the guide catheter disclosed in the attached provisional patent application entitled "Guide Catheter System", which modified version is discussed below).

3. Inflate the balloon 118 on the flow control catheter 111, occluding flow in the common carotid artery 61 and resulting in reversal of flow in the internal carotid artery 71 or cessation of flow (at the very least).

4. Load a micro-occlusion balloon catheter 80 containing a microwire through the selected angioplasty balloon catheter 90. (This will necessitate the placement of a microballoon on a microcatheter after loading, or the use of a proprietary device, currently in development.) Carefully navigate the micro-occlusion balloon 81 past the stenosis 40 with the angioplasty balloon 91 remaining proximal within the guide catheter lumen. The occluded common carotid artery 61 thus protects this initial dangerous crossing.

5. Before inflating the distal balloon 81, aspirate through the guide catheter 111 to remove any debris dislodged during the initial crossing of the plaque 40; any remainder will flow in a retrograde direction into the external carotid artery 72.

6. Inflate the distal micro-occlusion balloon 81, stopping all flow in the internal carotid artery 71.

7. Deflate the guide catheter occlusion balloon 118; this now allows the previously stagnant blood in the common carotid artery 61 to wash out into the external carotid artery 72 and refreshes this territory. It also further washes out the potentially disturbed stenotic region, with debris again going into the external carotid artery 72.

8. Reinflate the guide catheter occlusion balloon 118, ceasing flow in the common carotid artery 61.

9. Advance the angioplasty catheter 90 over the wire/ micro-occlusion balloon 80 into place and perform the angioplasty (and stent placement, if applicable).

10. Deflate the angioplasty balloon 91 and withdraw this catheter 90.

11. Slowly infuse contrast through the guide catheter 111 to visualize the angioplasty site.

12. Repeat if necessary (and place stent if necessary).

13. Open the external lumen of the guide catheter 111 to the air.

14. Deflate the distal occlusion balloon 81 and let back-bleeding occur for a few seconds, both into the external carotid artery 72 and out the guide catheter 111.

15. Close the external drainage of the guide catheter 111; let the retrograde flow from the internal carotid artery 71 continue into the external carotid artery 72. Perfuse with ReoPro, etc., as indicated.

16. Perform repeat angiogram to evaluate the status of the angioplasty site by injecting through the guide catheter lumen, slowly.

17. Remove all indwelling catheters/balloons except for the guide catheter 111.

18. Deflate the guide catheter balloon 118 and perform final angioplasty site evaluation.

19. Perform final evaluation of intracranial cerebral vasculature.

The preferred guide catheter system for getting the balloon catheter 111 to its intended location is the guide catheter system shown in FIGS. 17–23, but modified to include a balloon 118 on the guide catheter 111 disclosed herein. Thus, one could use the system shown in FIGS. 17–23, replacing the catheter 11 shown in FIGS. 17–23 with balloon catheter 111, which is the same as catheter 11 except that catheter 111 also includes a balloon 118 and means for inflating and deflating balloon 118.

PRODUCT:

The guide catheter design of the present invention incorporates design characteristics of a guide catheter with a method of introduction of the guide catheter into the vascular system and then into the target vessel all in one step.

PRODUCT DESCRIPTION:

TWO COMPONENTS:

1. A custom designed guide catheter 11, with a non-tapering inner and outer lumen size but with varying stiffness in the shaft tapering from a very stiff proximal shaft 13 to a very soft, atraumatic tip 12. Outer diameter of the guide will be non-tapering and can be from 5 fr. to 10 fr.

2. A custom made inner "dilator" 14 snugly hugging an 0.035 inch standard guidewire 21 and gradually expanding to fill the inner lumen of the guide catheter 11. This inner dilator 14 will be substantially longer than the guide catheter 11 and have a preshaped curve 15 to allow selection of vessels similar to the function of a standard diagnostic catheter. This dilator 14 will be used to introduce the guide catheter 11 through the skin. The inner dilator catheter 14 will extend approximately 10–30 cm past the tip 12 of the guide catheter 11 and be used to select the intended target vessel 61 of the guide catheter 11, just as a standard selecting diagnostic catheter would be used.

Figure 17:
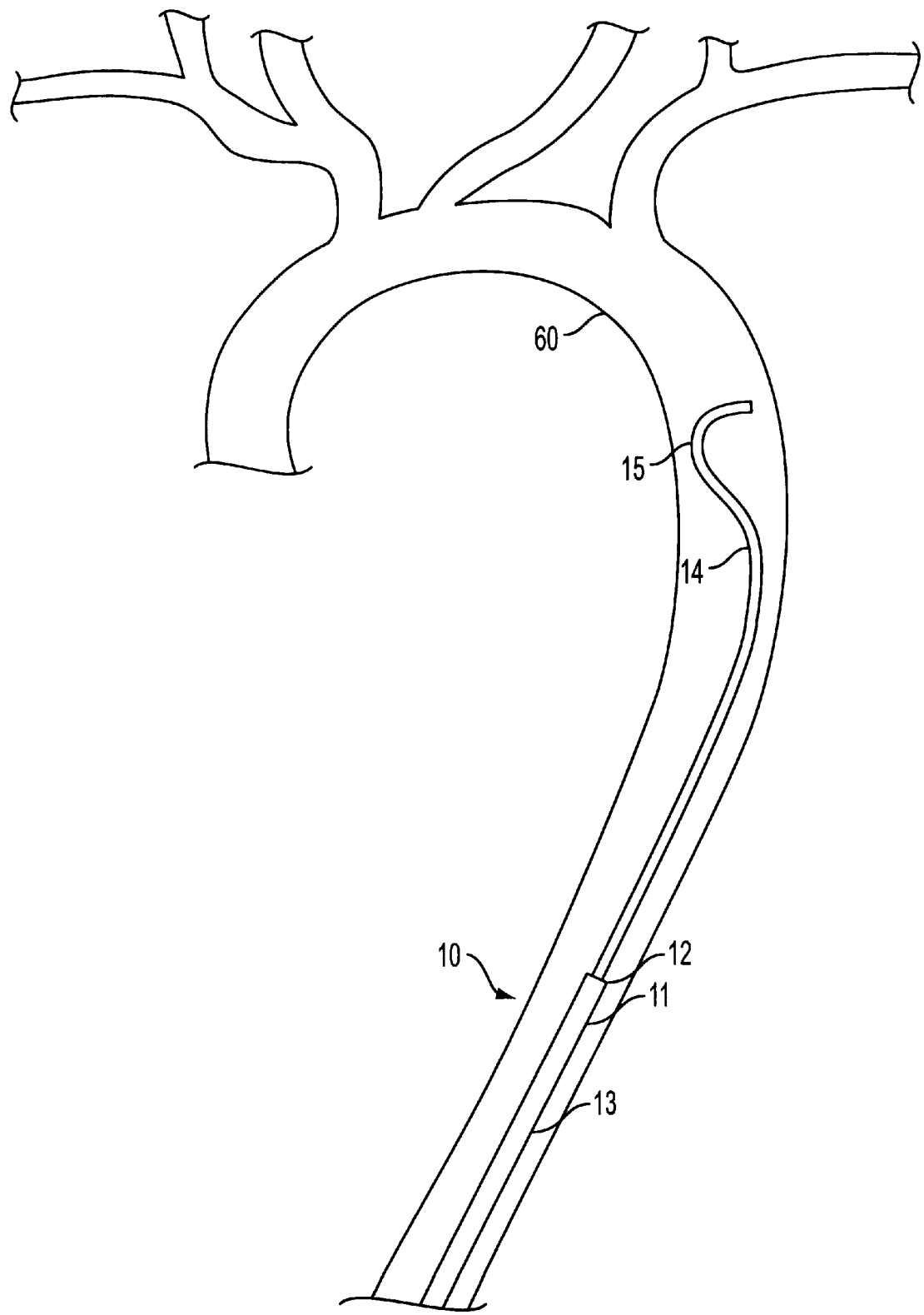
FIG. 17 is a schematic view of the vascular tree with the guide catheter system of the preferred embodiment of the apparatus of the present invention present therein.
Figure 18:
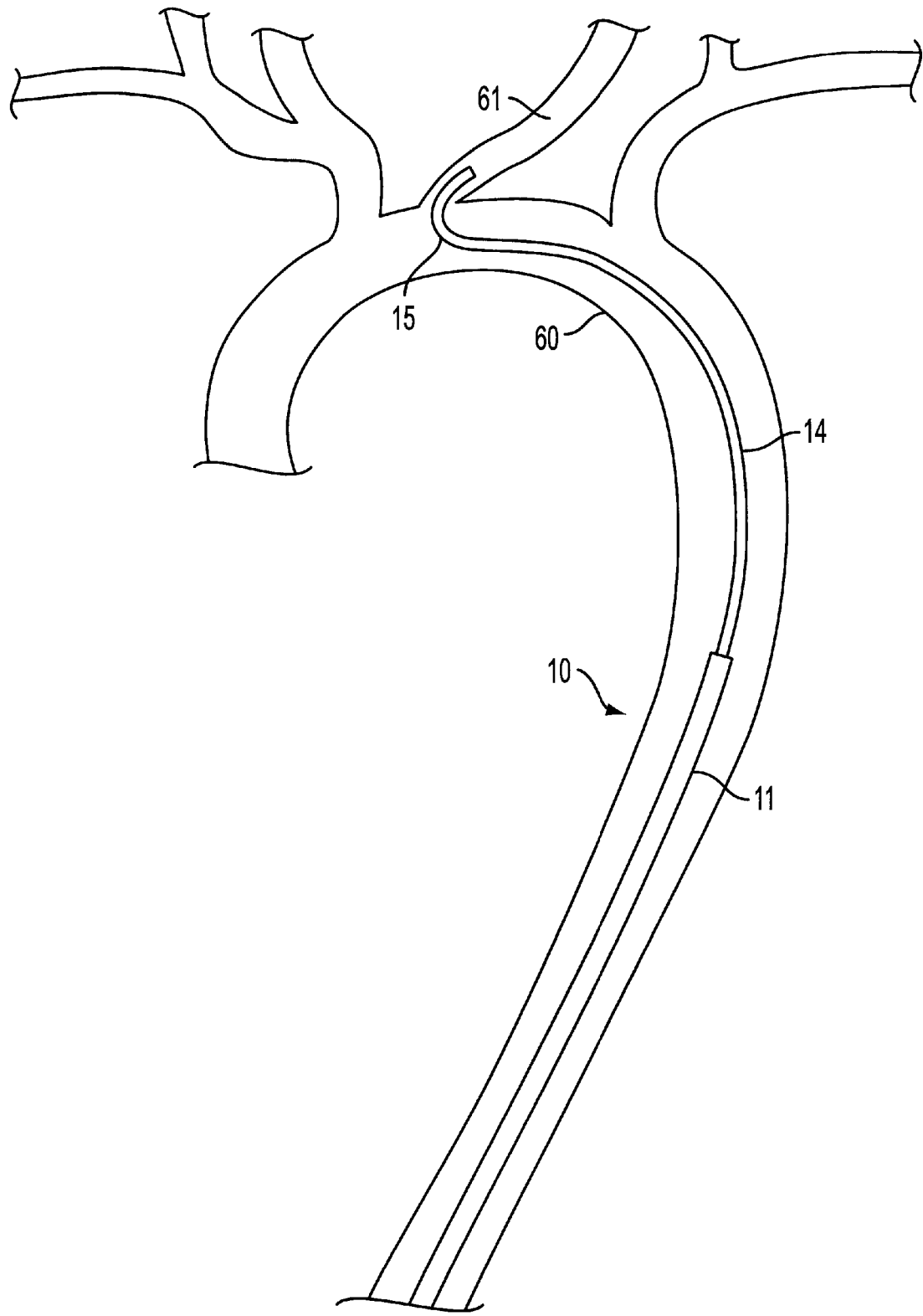
FIG. 18 is a schematic view showing the dilator selecting the origin of a blood vessel.
Figure 19:
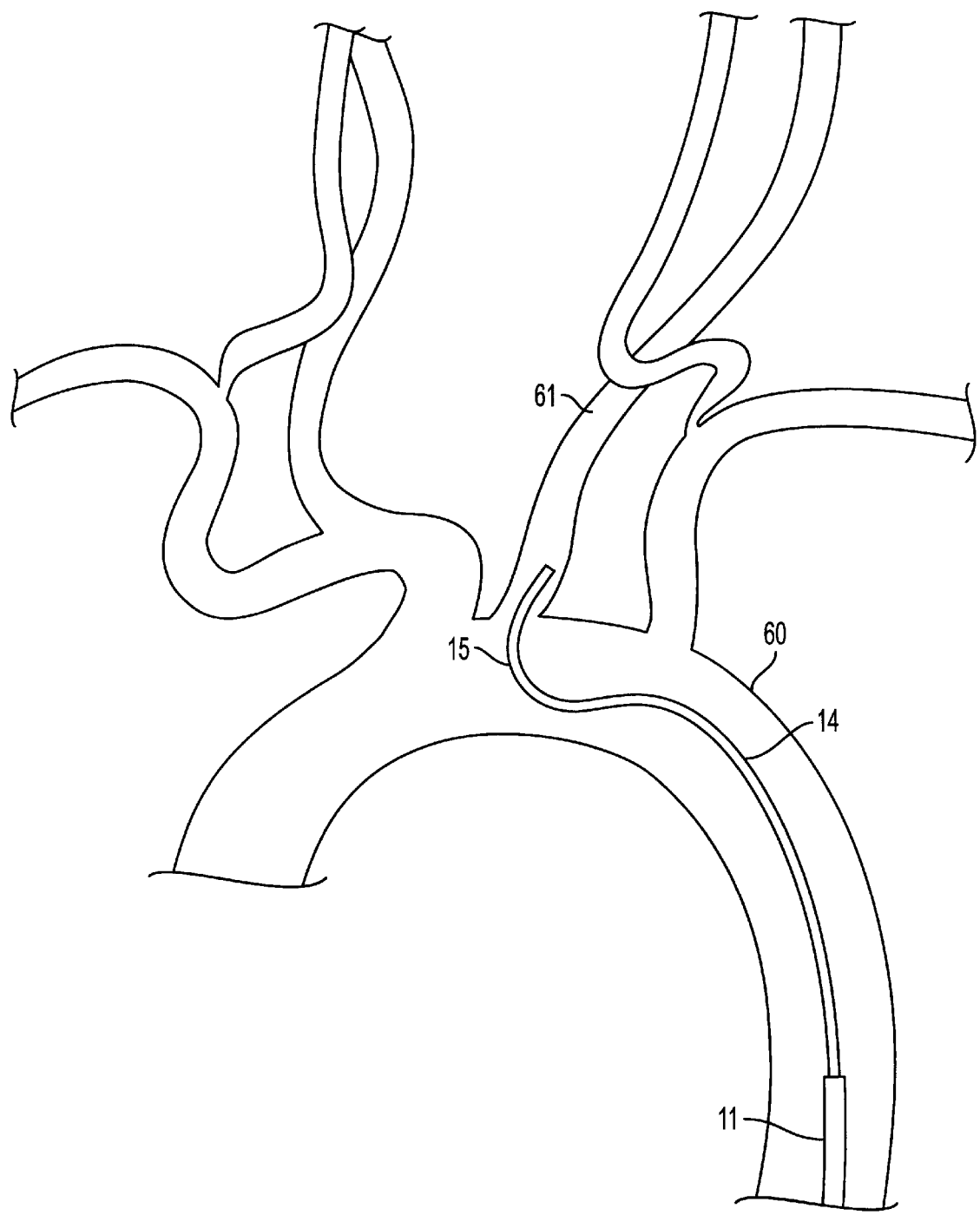
FIG. 19 is a close-up view similar to FIG. 18.
Figure 20:
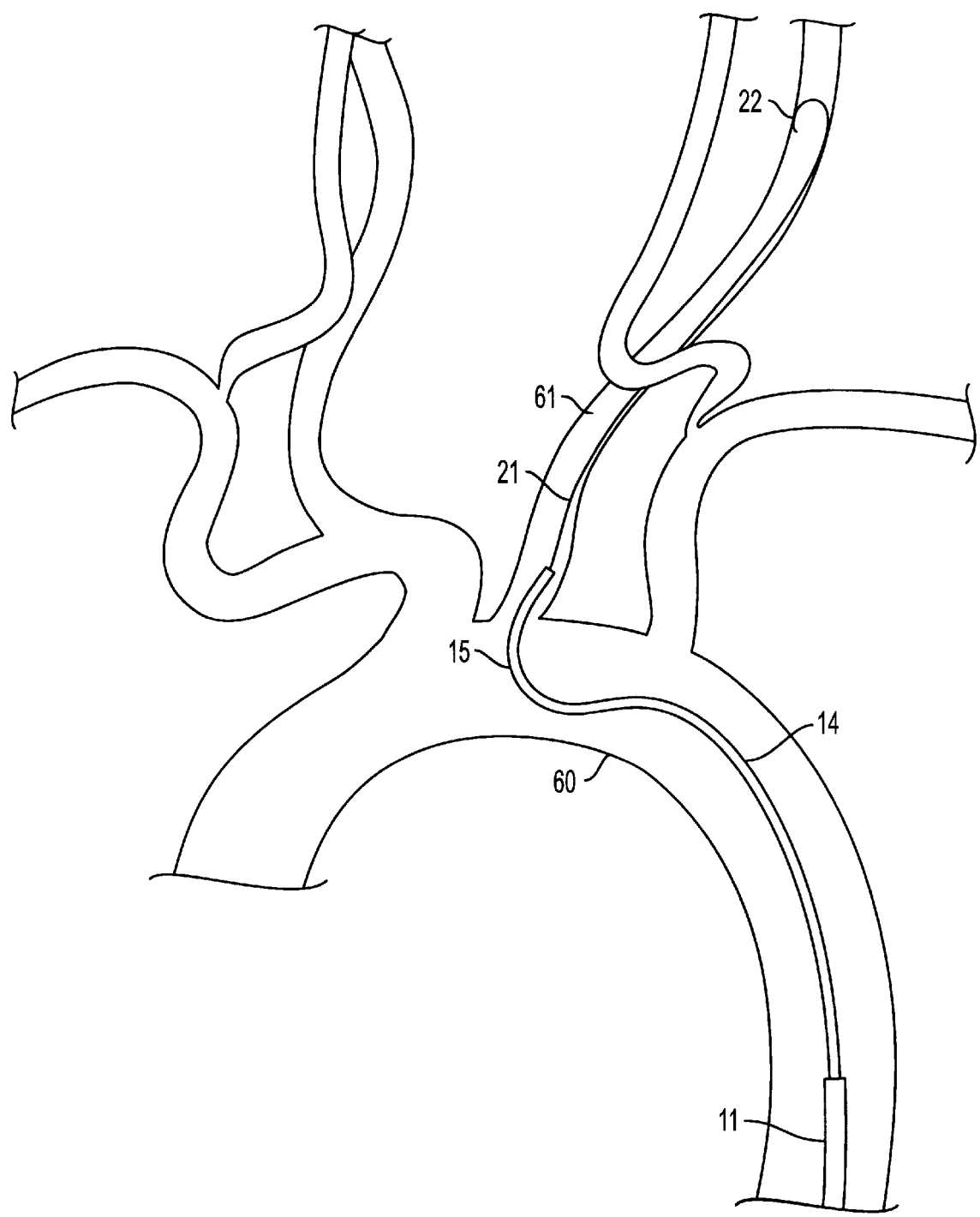
FIG. 20 is a view similar to FIG. 19, and showing the guidewire advanced into a distal blood vessel.
Figure 21:
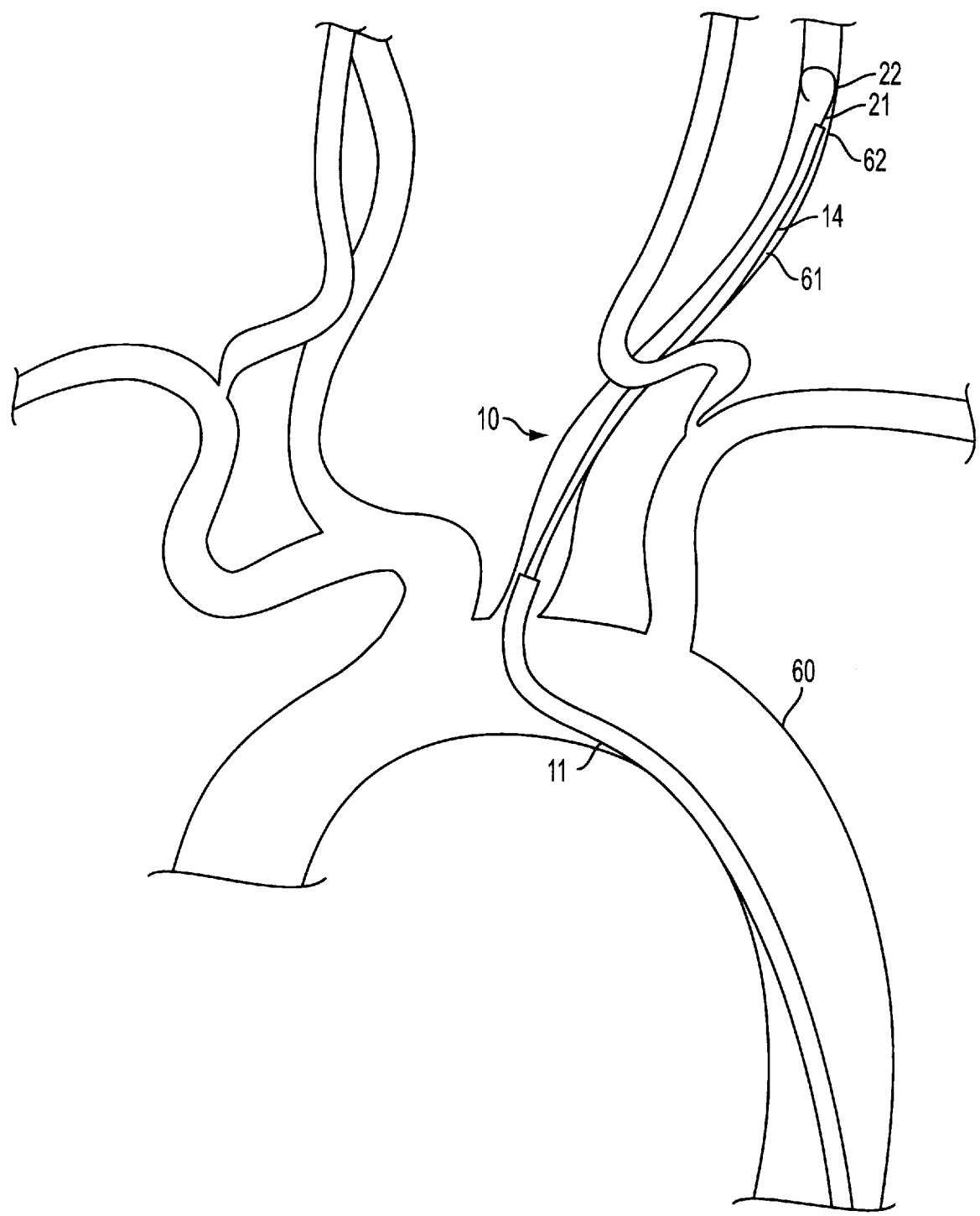
FIG. 21 shows the dilator/guide catheter unit of the preferred embodiment of the apparatus of the present invention in a position in which the inner dilator has reached its intended location.
Figure 22:
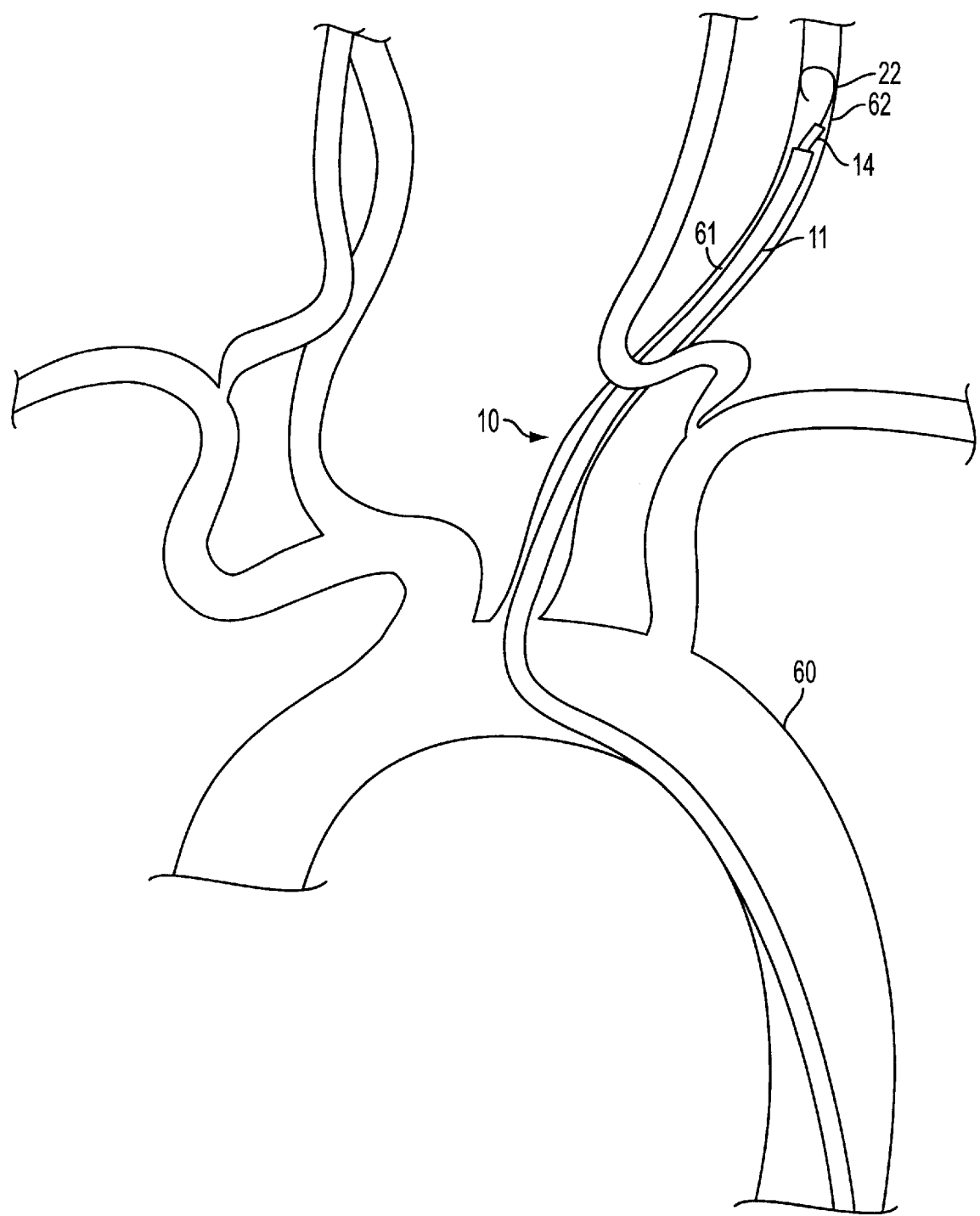
FIG. 22 shows the dilator/guide catheter unit of the preferred embodiment of the apparatus of the present invention where the guide catheter has been advanced over the inner dilator catheter to the intended location.
Figure 23:
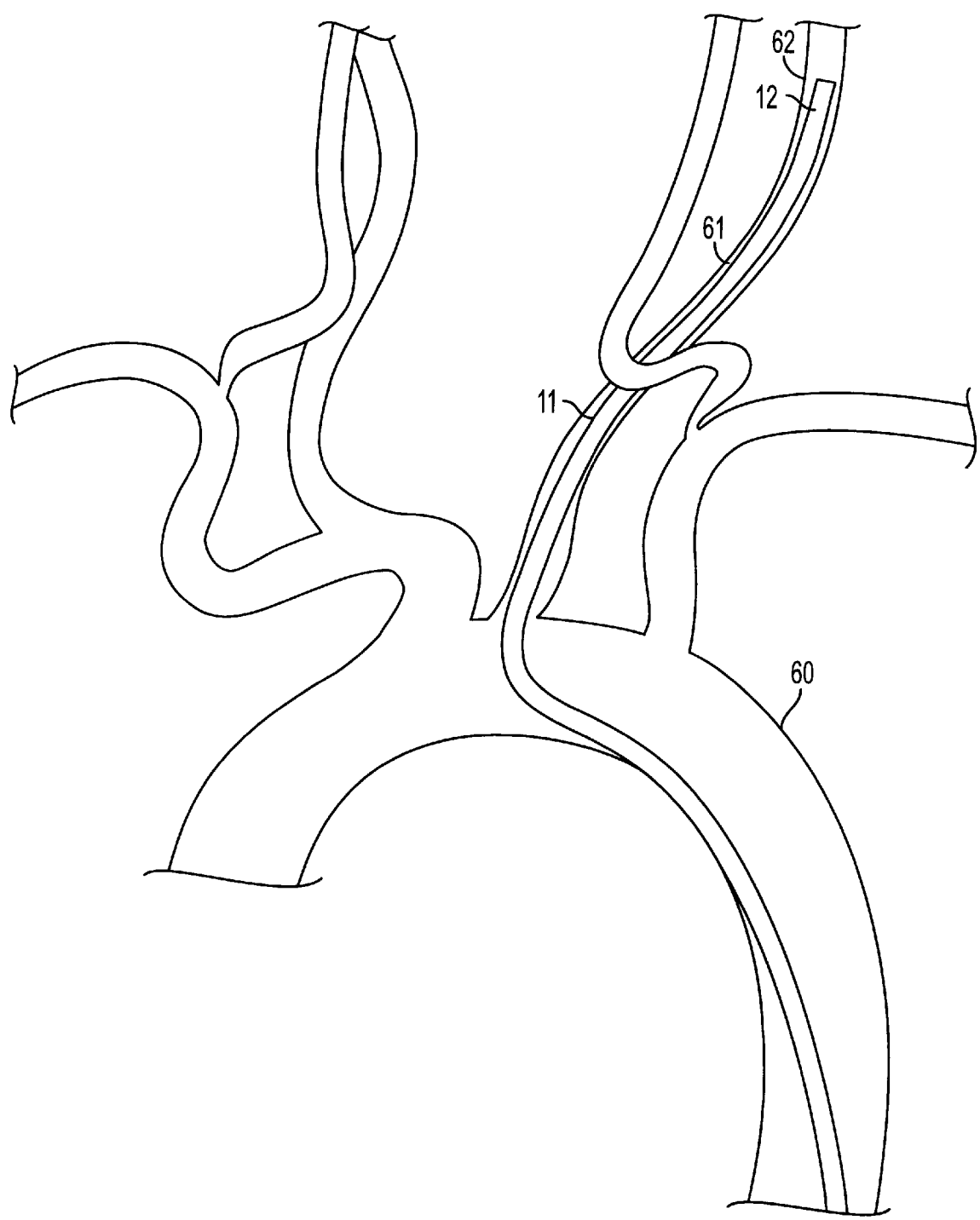
FIG. 23 is a view similar to FIG. 22, after the inner dilator and guidewire have been removed from the guide catheter.

DESCRIPTION OF USE:

The inner dilator 14 will extend from 10–30 cm past the guide catheter tip 12. This will be introduced over a standard guide wire 21 placed into the vascular tree 60 utilizing standard Seldinger technique. Once the wire 21 is in place, the dilator/guide catheter unit 10 will be slid over this wire 21 into place in the vascular tree 60 (FIG. 17). The intrinsic curve 15 of the inner dilator 14 will then be used to select the origin of a blood vessel 61 (FIGS. 18 and 19). A standard guidewire 21 will be placed through this into the distal blood vessel 61 (FIG. 20). The dilator/guide catheter unit 10 will be slid over this guidewire 21 until the inner dilator 14 has reached its intended location 62 (FIG. 21). The wire 21 and inner dilator 14 will be held in place and the guide catheter 11 advanced over this until it has reached its intended location 62 (FIG. 22). The inner dilator 14 and wire 21 will be pulled, leaving the guide catheter 11 in its intended location 62 (FIG. 23).

ADVANTAGES OVER STANDARD GUIDE CATHETER DESIGN:

1. The guide catheter can be introduced without the use of a large sheath, thus allowing the use of large guide catheters without a corresponding larger hole in the vessel wall.

2. The entire process of guide catheter introduction will be one process, thus much faster. The unit will be placed over a standard guide wire through the skin into the vasculature. The lack of need for a separate sheath system saves this step from the introducer.

3. The eventual target vessel for the guide catheter will be selected with a catheter/dilator specifically designed for that purpose (the inner "dilator"). This will allow optimal design capabilities for the guide catheter due to the fact that it will not have to function as a selecting catheter at the same time.

4. The lack of need for a separate diagnostic catheter to pre-select the intended vessel saves the step of placing a diagnostic catheter into the intended location, placing an exchange wire, pulling the selecting catheter, and then placing a guide catheter over this exchange wire.

Guide catheters these days are introduced generally through the body though a large sheath. And there are now some guide catheters which are introduced with a small thin dilator that leads them over a wire into the body, and one ends up with a guide catheter in the body that was gotten in there loaded over this little dilator. The present invention is a new system and technique for getting a guide catheter to the intended location which is described on the attached drawings (FIGS. 17–23). The tip of the dilator has been extended a considerable distance past the guide catheter itself so that now the tip of this dilator acts not only as a small introducing agent to follow the wire to get the guide catheter into the body, but also has the purpose of being able to select the vessel. So once one gets it into the vascular tree, one can fish downstream, select the vessel that is intended for the final location of the guide catheter. Once one has selected the vessel, then one uses a guide wire through it, just like with a standard diagnostic catheter. One places a wire downstream into the intended vessel, fishes the entire dilator/guide catheter system downstream into this vessel, and then once the dilator gets downstream, one pushes the entire guide catheter off it until it gets to its intended location down to where one wants to leave it. At that point, one pulls the wire and dilator back, leaving the guide catheter in place. Therefore, in basically one giant procedure, one introduces all of the catheter system through the skin, into the body, and up the vessel, into the final location. The advantage of getting the catheter into the selected vessel into its final location in one step is that one does not have to do any exchanges or use various materials being put into and out of the body and steps along the way to get the guide catheter to the place where one intends it to be.

This system allows one to do away with the sheath. It allows one to do away with a normal selecting diagnostic catheter to select the vessel. It allows one to do away with an exchange wire, or putting the exchange wire up into the vessel and then pulling the diagnostic catheter out and then putting the guide catheter in over the exchange wire and finally getting into position that way. So instead of having these multiple steps in the procedure, one basically have this one continuous step to get the guide catheter into the final location.

Typical dimensions for a guide catheter 11 of the present invention are as follows: length: 40–130 cm (90–100 cm, for example); outer diameter: 1.5–5 mm, preferably 5–12 fr. (6 french, for example); inner diameter: 4 fr.–10 fr.

Typical dimensions for a dilator catheter 14 of the present invention are as follows: length: 50–175 cm (about 20 cm longer than the guide catheter, for example); outer diameter: (sized to match the inner diameter of the guide catheter); inner diameter: sized to fit over a guide wire (0.040 inches, for example).

The curve 15 is chosen such that it aids in selecting the origin of the intended blood vessel. The radius of curvature of the curve 15 can be as in the Cook diagnostic cerebral catheters.

10 Parts list

10 guide catheter system

11 guide catheter

12 soft, atraumatic tip of guide catheter 11 (made of, for example, nylon or polyethylene)

13 very stiff proximal shaft of guide catheter 11 (made of, for example, braided, multilayer construction)

14 inner dilator catheter (made of, for example, nylon or polyethylene)

15 pre-shaped curve of inner dilator catheter 14
21 guidewire (Terumo stiff-shaft angle-tip glide wire commercially available from Terumo in Japan and distributed by Boston Scientific)
22 curved tip of guidewire 21
40 stenosis
50 stent (made of stainless steel and could be, e.g., a stent commercially available from Palmaz)
60 vascular tree
61 selected vessel (common carotid artery)
62 intended location of tip 112 of catheter 111 (or tip 12 of catheter 11)
71 internal carotid artery
72 external carotid artery
80 wire with balloon (e.g., a wire with balloon commercially available from Johnson & Johnson as part no. P104)
81 balloon of wire 80
90 angioplasty catheter (e.g., a Diamond™ brand angioplasty catheter commercially available from Boston Scientific having a balloon which is 6 mm in diameter by 20 mm long)
91 balloon of angioplasty catheter
110 guide catheter system
111 guide catheter (e.g., a catheter commercially available as FasGuide made by Target Therapeutic)
112 soft, atraumatic tip of guide catheter 111
113 very stiff proximal shaft of guide catheter 111

Enclosed is an appendix with more information about the present invention.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

What is claimed is:

1. A method of performing an operation including angioplasty of the internal carotid artery comprising the following steps:

(a) blocking flow in the common carotid artery, thus causing retrograde blood flow in the internal carotid artery;
   (b) blocking flow in the internal carotid artery, distal of a stenosis;
   (c) performing angioplasty on the stenosis;
   (d) unblocking flow in the internal carotid artery, thus allowing retrograde blood flow in the internal carotid artery into the external carotid artery; and
   (e) unblocking flow in the common carotid artery.

* * * * *